(12) United States Patent
Benchikh et al.

(10) Patent No.: US 9,079,964 B2
(45) Date of Patent: Jul. 14, 2015

(54) IMMUNOASSAY FOR CYCLOPROPYLINDOLE BASED SYNTHETIC CANNABINOIDS, METABOLITES AND DERIVATIVES THEREOF

(71) Applicant: Randox Laboratories Limited, Crumlin (GB)

(72) Inventors: Elouard Benchikh, Crumlin (GB); Ivan McConnell, Crumlin (GB); Philip Lowry, Crumlin (GB); Peter Fitzgerald, Crumlin (GB)

(73) Assignee: RANDOX LABORATORIES LIMITED, Crumlin (GB)

( * ) Notice: Subject to any disclaimer, the term of this patent is extended or adjusted under 35 U.S.C. 154(b) by 0 days.

(21) Appl. No.: 14/067,752

(22) Filed: Oct. 30, 2013

(65) Prior Publication Data

US 2014/0287441 A1  Sep. 25, 2014

(30) Foreign Application Priority Data

Mar. 20, 2013  (GB) .................................. 1305061.2

(51) Int. Cl.
C07K 16/00 (2006.01)
C07K 1/04 (2006.01)
G01N 33/53 (2006.01)
C07K 16/44 (2006.01)
G01N 33/94 (2006.01)

(52) U.S. Cl.
CPC .............. *C07K 16/44* (2013.01); *G01N 33/948* (2013.01); *C07K 2317/33* (2013.01)

(58) Field of Classification Search
CPC .... C07K 16/16; C07K 16/44; C07K 2317/33; G01N 33/948; C07D 209/04
See application file for complete search history.

(56) References Cited

U.S. PATENT DOCUMENTS

| 6,046,138 A * | 4/2000 | Yokoyama et al. ........... 504/284 |
| 2012/0208213 A1 | 8/2012 | Benchikh et al. |
| 2013/0065323 A1 | 3/2013 | Benchikh et al. |
| 2013/0066053 A1 | 3/2013 | Fitzberald et al. |
| 2013/0196354 A1 | 8/2013 | Fitzgerald et al. |

FOREIGN PATENT DOCUMENTS

EP  2 487 155 A1  8/2012

OTHER PUBLICATIONS

Goodrow et al. Strategies for Immunoassay hapten design. In Immunoanalysis of Agrochemicals; Nelson, J., et al.; ACS symposium Series; American Chemical Society: Washington, DC, 1995, pp. 119-139.*
Nolli et al. Antibodies against the antibiotics: an overview. Ann. 1st. Super. Sanita., vol. 27, No. 1, pp. 149-154.*
Vearrier et al. Biological testing for drugs of abuse. Molecular, Clinical and Environmental Toxicology., 2010, vol. 2, pp. 489-517.*

(Continued)

*Primary Examiner* — Shafiqul Haq
(74) *Attorney, Agent, or Firm* — Seed IP Law Group PLLC

(57) ABSTRACT

The invention relates to the detection and quantification of cyclopropylindole based synthetic cannabinoids UR-144 and XLR-11 by providing antibodies based on novel immunogens. These antibodies can be incorporated into methods and kits for the detection of UR-144, XLR-11 and their metabolites.

25 Claims, 6 Drawing Sheets

(56) References Cited

OTHER PUBLICATIONS

Nolli et. al. Antibodies against antibiotics: an overview. Ann. Ist. Super. Sanita., 1991, vol. 27, No. 1, pp. 149-154.*

"Synthetic Cannabinoids and Metabolites (Spice) ELISA," web page at randoxtoxicology.com/Products/Elisa-p-50 downloaded Mar. 14, 2014, 1 page.

Kavanagh et al., "UR-144 in products sold via the Internet: Identification of related compounds and characterization of pyrolysis products," *Drug Testing and Analysis* (www.drugtestinganalysis.com) DOI 10.1002/dta.1456, 10 pages, 2013.

Schwartz et al., "Acute Kidney Injury Associated with Synthetic Cannabinoid Use—Multiple States, 2012," *Centers for Disease Control and Prevention MMWR* 62(6):93-98, 2013.

Sobolevsky et al., "Detection of urinary metabolites of AM-2201 and UR-144, two novel synthetic cannabinoids," *Drug Testing and Analysis* 4:745-753, 2012.

Uchiyama et al., "URB-754: A new class of designer drug and 12 synthetic cannabinoids detected in illegal products," *Forensic Science International* http://dx.doi.org/10.1016/j.forsciint.2012.08.047, 12 pages, 2012.

* cited by examiner

UR-144　　　　　　　　　XLR-11

IMMUNOASSAY FOR CYCLOPROPYLINDOLE BASED SYNTHETIC CANNABINOIDS, METABOLITES AND DERIVATIVES THEREOF

CROSS-REFERENCE TO RELATED APPLICATION

This application claims the benefit under 35 U.S.C. §119 (a) of United Kingdom (GB) Patent Application No. 1305061.2 filed Mar. 20, 2013, which is incorporated herein by reference in its entirety.

BACKGROUND

New designer drugs are often created as alternatives to existing illegal drugs precisely with the intention that they can be sold and marketed with the appearance of legality.

Synthetic cannabinoids, which have similar pharmacology to Tetrahydrocannabinol (THC) the psychoactive ingredient in cannabis, originated as part of research into the cannabinoid receptors $CB_1$ and $CB_2$. Due to their activity at these receptors they have been exploited by drug traffickers and users as legal alternatives to cannabis. Synthetic cannabinoids are generally packaged and sold (under names such as Spice, K2 and herbal incense) as a mixture of an organic carrier medium, usually plant material, which is typically sprayed or mixed with the synthetic compound.

Many of the original compounds commonly found in these mixtures, including JWH-018 and JWH-073, have now been scheduled as illegal drugs in many countries. Clandestine manufacturers and traffickers have responded to these changes in legality simply by producing and distributing synthetic cannabinoid products containing slightly varied compounds in attempts to circumvent these newly created laws.

Among the most recently identified compounds are UR-144 and XLR-11 (Sobolevsky et al 2012; Uchiyama et al 2012; Kavanagh et al 2013). UR-144 and XLR-11 are the new generation of synthetic cannabinoids and are chemically different to the first generation cannabinoids. The napthlene ring in JWH-018 (first generation cannabinoids) is substituted with a tetramethylcyclopropyl group to form UR-144. XLR-11 is the fluorinated version of UR-144. UR-144 ((1-pentyl-1H-indol-3-yl)(2,2,3,3-tetramethylcyclopropyl)-methanone) is a potent synthetic cannabinoid with preferential binding to the peripheral $CB_2$ receptor over the central $CB_1$ receptor. UR-144 has high affinity for the $CB_2$ receptor with a Ki of 1.8 nM but 83× lower affinity for the $CB_1$ receptor with a Ki of 150. XLR-11 ((1-(5-fluoropentyl)-1H-indol-3-yl)(2,2,3,3-tetramethylcyclopropyl) methanone) is an aminoalkylindole compound that is expected to be a cannabinoid mimetic. It is reported that the tetramethylcyclopropyl group confers selectivity for the $CB_2$ over $CB_1$ receptor however the N-(5-fluoropentyl) chain increases binding to both receptors.

UR-144 was added to a temporary class drug schedule in New Zealand on 6 Apr. 2012, while XLR-11 was also added on 13 Jul. 2012. From 11 Dec. 2012 both UR-144 and XLR-11 have been banned in the US state of Florida.

The pharmacological and toxicological effects of many of these synthetic compounds in humans are unknown and unpredictable. They have been reported to cause agitation, anxiety, nausea, vomiting, tachycardia, elevated blood pressure, tremor, seizures, hallucinations, paranoid behaviour and non-responsiveness. XLR-11 and its metabolites have been proposed as the cause in cases of unexplained acute kidney injury (Schwartz et al, 2013).

Current analytical methods use mass-spectrometry (MS) in conjunction with gas chromatography (GC) or liquid chromatography (LC). A disadvantage of such methods of detection is that they require expensive equipment and highly trained staff.

On the other hand, immunoassays are known in the art as relatively cost effective, simplistic and rapid alternatives to mass-spectrometry based analysis. European patent application number 2,487,155 provides immunoassay based methods for the detection of the JWH and CP families of synthetic cannabinoids, however, the antibodies provided in this application show no significant cross-reactivity to UR-144, its metabolites or derivatives. Therefore, there remains a need for an assay which is not only sensitive to the parent molecules of UR-144 and XLR-11 but that can also detect their key metabolites and derivatives to enable improvements in the forensic toxicological and clinical analysis of the intake of these ever evolving designer drugs.

References

Sobolevsky et al., (2012) Drug Testing and Analysis, 4:745-753.

Uchiyama et al., (2012) Forensic Science International, doi:10.1016/j.forsciint.2012.08.047

Schwartz et al., (2013) Centers for Disease Control and Prevention, MMWR; 62:93-98.

Kavanagh et al., (2013) Drug Testing and Analysis, doi: 10.1002/dta.1456

BRIEF SUMMARY

Provided herein are haptens, immunogens and antibodies useful in detecting cyclopropylindole based synthetic cannabinoids. The antibodies can be incorporated into methods, assays and kits for the detection of cyclopropylindole based synthetic cannabinoids, specifically UR-144, XLR-11 and/or their metabolites.

In one embodiment, an antibody is provided that is capable of binding to at least one epitope having the general formula (I):

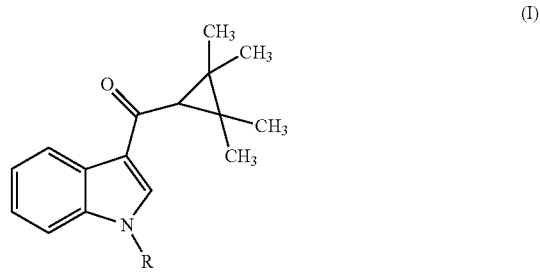

wherein, R is H or a $C_1$-$C_6$ substituted or unsubstituted hydrocarbon chain. In certain embodiments, R is selected from H, substituted methyl, substituted ethyl, substituted or unsubstituted propyl, substituted or unsubstituted butyl, substituted or unsubstituted pentyl, or substituted and unsubstituted hexyl. In another embodiment, R is a substituted alkyl group. In a more specific embodiment, R is a substituted pentyl group. In still another specific embodiment, R is selected from pentyl, 5-hydroxypentyl, 4-hydroxypentyl, pentanoic acid, and 5-fluoropentyl. In a certain specific embodiment, R is pentanoic acid or an amide or ester derivative thereof. In another specific embodiment, R is a substituted methyl group. In another embodiment, R is a substituted methyl group in which methyl is substituted with substituted or substituted, saturated or unsaturated pyran. In yet another specific embodiment, R is a substituted methyl group in which methyl is substituted with tetrahydropyran. In one embodiment, the antibody provided herein is capable of binding to at least one epitope of an analyte selected from UR-144, UR-144 pentanoic acid, UR-144 N-pentanol, UR-144 desalkyl and/or XLR-11 and/or metabolites or derivatives thereof. In certain embodiments, the antibody has 100% cross-reactivity to UR-144 pentanoic acid and greater than 10% cross-reactivity to UR-144, UR-144 N-pentanol, UR-144 desalkyl and XLR-11. In other certain embodiments, the antibody has 100% cross-reactivity to UR-144 pentanoic acid and greater than 15% cross-reactivity to UR-144, UR-144 N-pentanol, UR-144 desalkyl and XLR-11. In certain embodiments, the antibody has 100% cross-reactivity to UR-144 pentanoic acid and greater than 100% cross-reactivity to UR-144 N-pentanol. In another embodiment, the antibody is further characterised in that the antibody shows no significant binding to JWH-098, JWH-022, JWH-398, JWH-210, JWH-018 (6-hydroxyindole), JWH-018 (5-hydroxyindole), JWH-018 N (5-hydroxypentyl) metabolite, RCS-4, RCS-8, AM-1220, AM-2201, AM-694, AM-1241, JWH-015, JWH-200, JWH-073, JWH-019, JWH-018, JWH-250 and/or JWH-018 (N-carboxybutyl) metabolite. In a more specific embodiment, the antibody has an $IC_{50}$ selected from one or more of at least 3.484 ng/ml for UR-144 N-pentanoic acid, 22.815 ng/ml for UR-144, 3.191 ng/ml for UR-144 N-pentanol, 19.207 ng/ml for UR-144 desalkyl and 9.454 ng/ml for XLR-11.

In another embodiment, also provided herein is an immunoassay method for detecting or quantifying UR-144, UR-144 pentanoic acid, UR-144 N-pentanol, UR-144 desalkyl, XLR-11 and/or metabolites thereof in a sample, the method comprising the steps of (a) providing a mixture of the sample, the antibody as described above and herein, and a conjugate of structure II Structure II

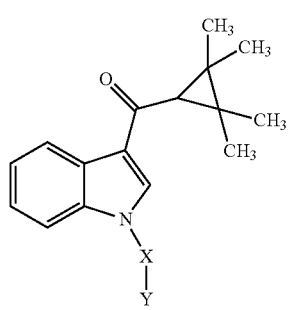

in which X is an organic spacing group and Y is a labelling agent which is detectable; (b) allowing the antibody to bind to the conjugate and any UR-144, UR-144 pentanoic acid, UR-144 N-pentanol, UR-144 desalkyl, XLR-11 and/or metabolites thereof present in the sample; and (c) detecting the presence of or measuring the amount of conjugate bound to the antibody, the presence or amount of conjugate indicating the presence or amount of UR-144, UR-144 pentanoic acid, UR-144 N-pentanol, UR-144 desalkyl, XLR-11 and/or metabolites thereof in the sample. In a particular embodiment, X of structure II is -Q-Z—, in which Z, attached to N, is a crosslinking group selected from a $C_1$-$C_{10}$, preferably a $C_1$-$C_5$, substituted or unsubstituted straight or branched chain, saturated or unsaturated alkylene moiety; and Q is (before conjugation to Y) a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof. In yet another embodiment, Y is selected from an enzyme, a luminescent substance, a radioactive substance or a mixture thereof.

In another embodiment, provided herein is an antibody that is raised against an immunogen, wherein the immunogen comprises formula (I) conjugated to an antigenicity-conferring carrier material (accm):

(I)

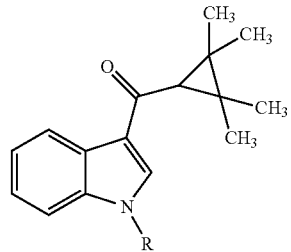

wherein, R is H or a $C_1$-$C_6$ substituted or unsubstituted hydrocarbon chain, and the antibody is able to bind an epitope of an analyte selected from UR-144, UR-144 pentanoic acid, UR-144 N-pentanol, UR-144 desalkyl and/or XLR-11 and/or metabolites or derivatives thereof. In certain embodiments, the immunogen comprises formula (I) directly conjugated to an antigenicity-conferring carrier material (accm). In a particular embodiment, the immunogen comprises formula (I) conjugated to an antigenicity-conferring carrier material (accm) via a cross-linking group selected from a carboxyl, dithiopyridyl, maleimidyl, amino, hydroxyl, thiol, and aldehyde moiety. In another particular embodiment, the antigenicity-conferring carrier material (accm) is selected from selected from bovine serum albumin (BSA), egg ovalbumin, bovine gamma globulin, bovine thyroglobulin (BTG), keyhole limpet haemocyanin (KLH), synthetic poly(amino acids) having a sufficient number of available amino groups, lysine, and synthetic or natural polymeric materials bearing reactive functional groups. In still another embodiment, the antibody is derivable from an immunogen consisting of either UR-144 N-pentanoic acid or UR-144 N-pentanoic acid HCTL conjugated to an antigenicity-conferring carrier material.

In still another embodiment, an immunoassay method is provided herein for detecting or quantifying UR-144, UR-144 pentanoic acid, UR-144 N-pentanol, UR-144 desalkyl, XLR-11 and/or metabolites thereof in a sample, the method comprising the steps of (a) providing a mixture of the sample, the antibody described above and herein and a conjugate of structure II Structure II

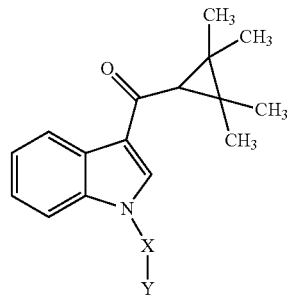

in which X is an organic spacing group and Y is a labelling agent which is detectable; (b) allowing the antibody to bind to the conjugate and any UR-144, UR-144 pentanoic acid, UR-144 N-pentanol, UR-144 desalkyl, XLR-11 and/or metabolites thereof present in the sample; and (c) detecting the presence of or measuring the amount of conjugate bound to the antibody, the presence or amount of conjugate indicating the presence or amount of UR-144, UR-144 pentanoic acid, UR-144 N-pentanol, UR-144 desalkyl, XLR-11 and/or metabolites thereof in the sample. In particular embodiments, X of structure II is -Q-Z—, in which Z, attached to N, is a crosslinking group selected from a $C_1$-$C_{10}$, preferably a $C_1$-$C_5$, substituted or unsubstituted straight or branched chain, saturated or unsaturated alkylene moiety; and Q is (before conjugation to Y) a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof. In another particular embodiment, Y is selected from an enzyme, a luminescent substance, a radioactive substance or a mixture thereof.

DETAILED DESCRIPTION

Figure 1:
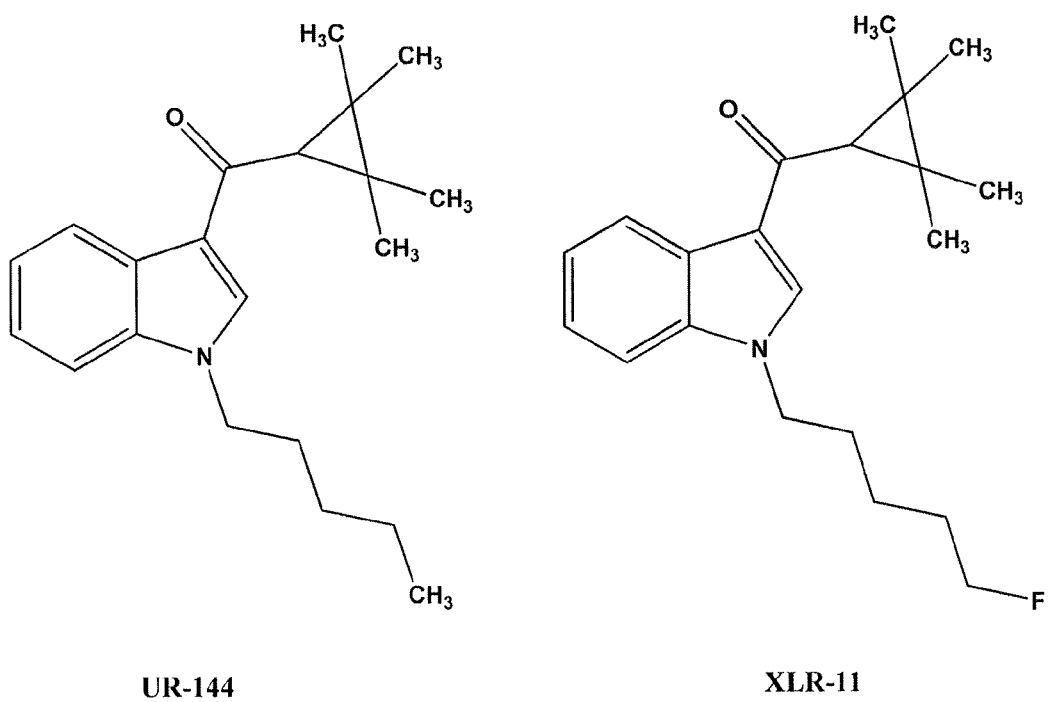
FIG. 1: Chemical structures of Synthetic Cannabinoids UR-144 and XLR-11

The invention provides haptens, immunogens and antibodies which are useful in detecting cyclopropylindole based synthetic cannabinoids. These antibodies can be incorporated into methods, assays and kits for the detection of cyclopropylindole based synthetic cannabinoids, specifically UR-144, XLR-11 and/or their metabolites.

Unless otherwise stated technical terms as used herein are used according to the conventional usage as known to those skilled in the art.

UR-144 as used herein refers to a chemical compound with the formal name (1-pentyl-1H-Indol-3-yl)(2,2,3,3-tetramethylcyclopropyl) methanone and Chemical Abstracts Service (CAS) registry number 1199943-44-6.

XLR-11 as used herein refers to a chemical compound with the formal name (1-(5-fluoropentyl)-1H-Indol-3-yl)(2,2,3,3-tetramethylcyclopropyl) methanone and CAS registry number 1364933-54-9.

The term "hapten" as used herein describes a pre-immunogenic molecule that stimulates antibody production only when conjugated to a larger carrier molecule. Once the hapten is conjugated to the antigenicity-conferring carrier material (accm) it forms the immunogen.

The term "immunogen" as used herein, describes an entity that induces an immune response such as production of antibodies or a T-cell response in a host animal.

The accm can be any material that makes all or part of the hapten susceptible to antibody recognition and binding. For example the accm can be a protein, a protein fragment, a synthetic polypeptide or a semi-synthetic polypeptide. Illustrative examples of useful antigenicity-conferring carrier materials are bovine serum albumin (BSA), egg ovalbumin, bovine gamma globulin, bovine thyroglobulin (BTG), keyhole limpet haemocyanin (KLH) etc. Preferably, the accm is BSA or BTG.

The term "antibody" as used herein refers to an immunoglobulin or immunoglobulin-like molecule. It will be understood that any type of immunoglobulin molecule or fragment thereof can be used, for example monoclonal antibodies, Fab fragments, scFv fragments and any other antigen binding fragments.

When used in reference to an antibody, the word 'specific' or 'specificity' in the context of the current invention refers to the analyte that is preferably bound by the antibody, as gauged by a suitable metric such as the cross-reactivity, i.e., the analyte with the greatest cross-reactivity is the antibody specific analyte and is generally given a value of 100%, with all other analytes accorded a value relative to this; in addition, as is known by one skilled in the art, for cross-reactivity to be of practical use the analyte specific antibody must display a high sensitivity as measured by a suitable metric such as the $IC_{50}$. The $IC_{50}$ is a common measure of antibody sensitivity for immunoassays.

According to a general aspect of the invention there is provided a hapten having the general formula

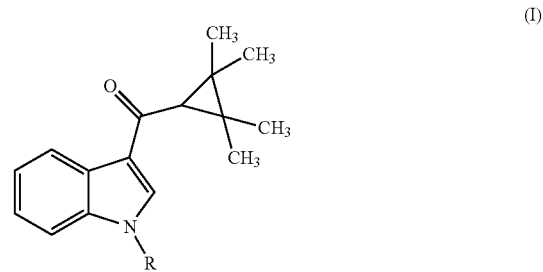

(I)

wherein, R is H or a $C_1$-$C_6$ substituted or unsubstituted hydrocarbon chain. Preferably, R is a substituted hydrocarbon chain, more preferably a substituted alkyl group. These aspects of the invention are expanded on below.

According to another general aspect of the invention, there is provided an immunogen having the formula (I) conjugated to an antigenicity-conferring carrier material (accm)

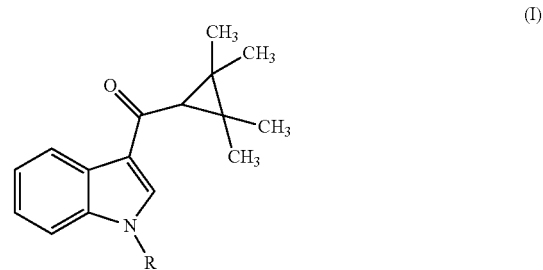

(I)

wherein, R is H or a $C_1$-$C_6$ substituted or unsubstituted hydrocarbon chain. Preferably, R is a substituted hydrocarbon chain, more preferably a substituted alkyl group. Conjugation may take place directly or with a cross-linking group. These aspects of the invention are expanded on below.

A first general aspect of the invention is an antibody which binds or is capable of binding to at least one epitope having the formula (I):

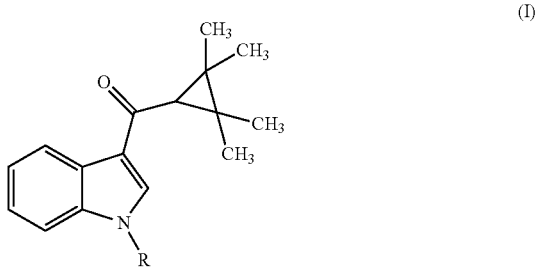
(I)

wherein, R is H or a $C_1$-$C_6$ substituted or unsubstituted hydrocarbon chain. Preferably, R is a substituted hydrocarbon chain, more preferably a substituted alkyl group.

A second general aspect of the invention is an antibody derivable from or raisable against an immunogen, in which the immunogen comprises a hapten conjugated to an accm, and wherein the hapten has the formula (I):

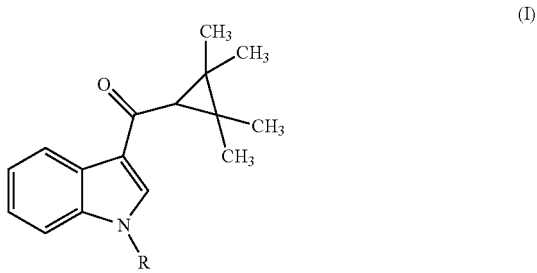
(I)

wherein, R is H or a $C_1$-$C_6$ substituted or unsubstituted hydrocarbon chain. Preferably, R is a substituted hydrocarbon chain, more preferably a substituted alkyl group. Conjugation may take place directly or with a cross-linking group. These aspects of the invention are expanded on below.

Figure 4:
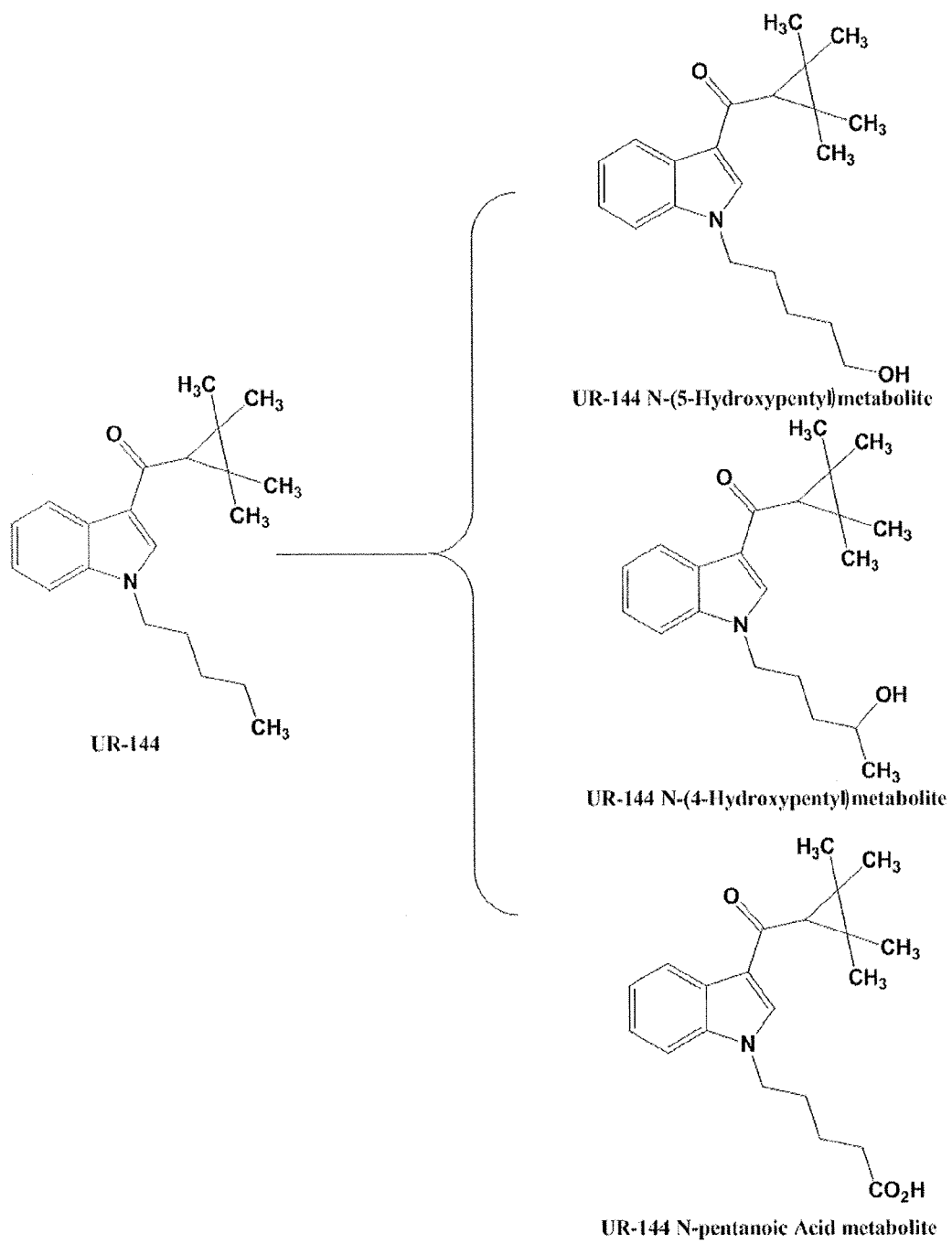
FIG. 4: The main metabolites of UR-144

In both of these antibody embodiments, the antibody is able to bind at least one epitope of formula (I). In this manner the antibody of the invention is able to bind an epitope of an analyte selected from UR-144, UR-144 pentanoic acid, UR-144 N-pentanol, UR-144 desalkyl and/or XLR-11 and/or metabolites or derivatives thereof. Metabolites of UR-144 and XLR-11 are shown in FIGS. 4 and 5.

Ideally, the antibody is specific for UR-144 N-pentanoic acid.

Figure 5:
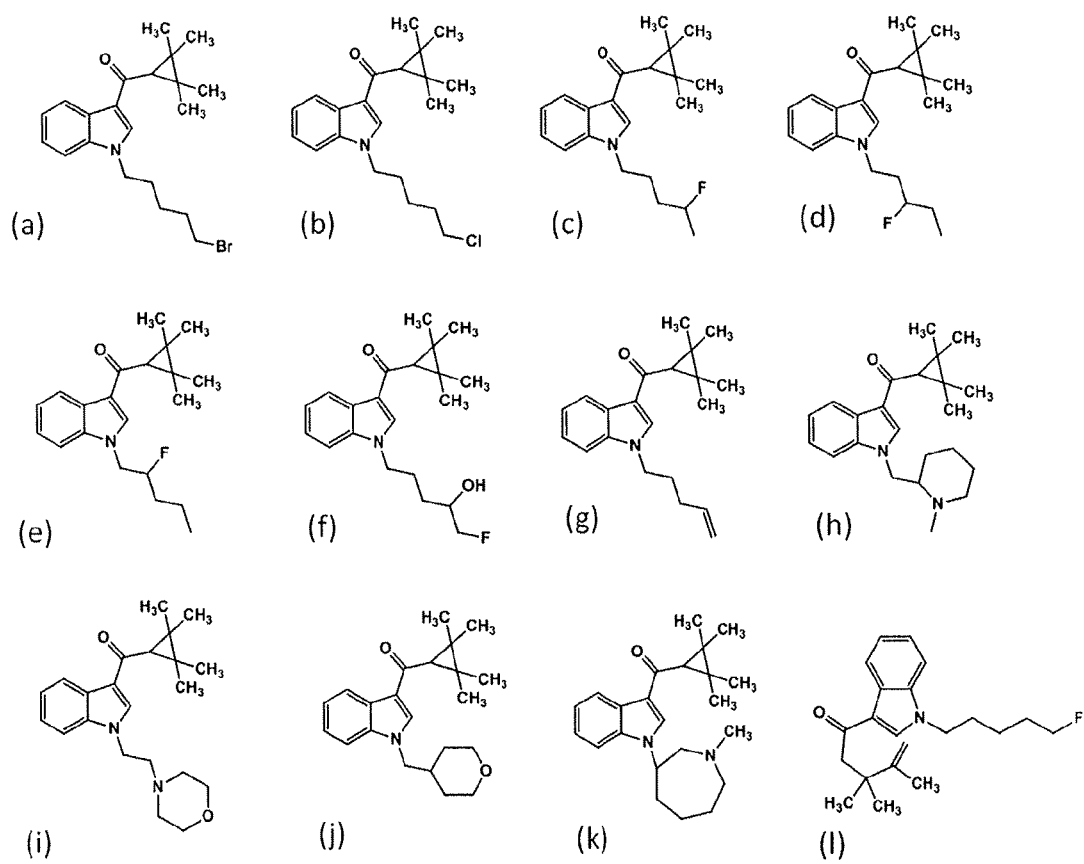
FIG. 5: Chemical structures of additional metabolites and derivatives of UR-144 and XLR-11; (a) UR-144 N-(5-bromopentyl) analog, (b) UR-144 N-(5-chloropentyl) analog, (c) XLR-11 N-(4-fluoropentyl) isomer, (d) XLR-11 N-(3-fluoropentyl) isomer, (e) XLR-11 N-(2-fluoropentyl) isomer, (f) XLR-11 N-(4-hydroxypentyl) metabolite, (g) XLR-11 N-(4-pentenyl) analog, (h) AB-005, (i) AB-796260, (j) A-834735, (k) AB-005 Azepane isomer, (l) XLR-11 Degradant.
Figure 6:
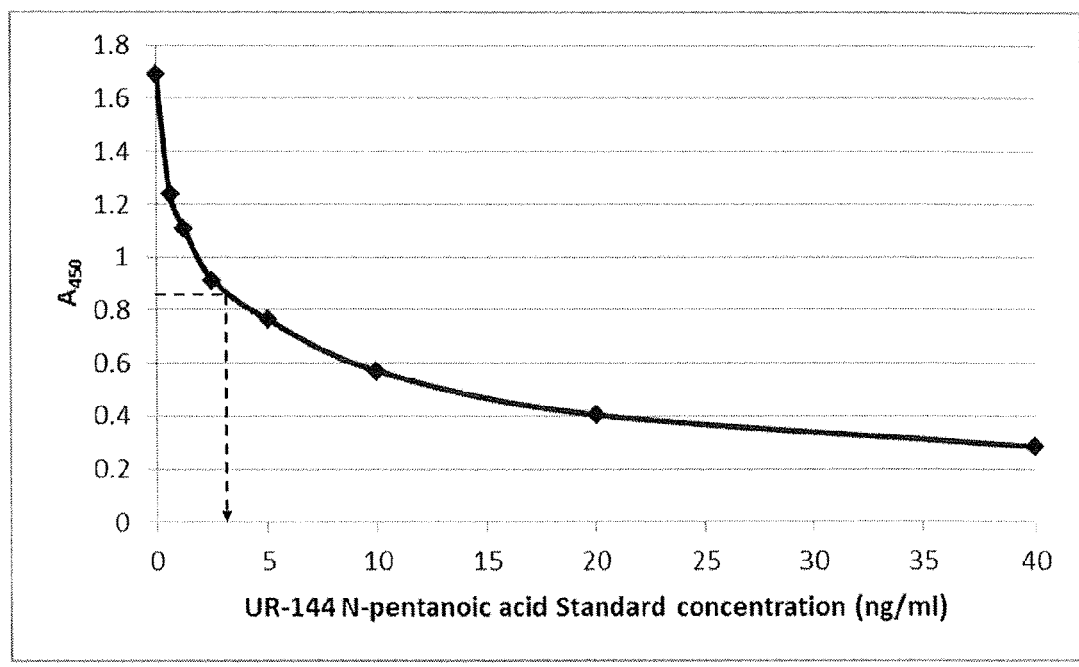
FIG. 6: Calibration curve showing absorbance at 450 nm using UR-144 N-pentanoic acid as the standard in an ELISA incorporating antiserum raised from immunogen I (The dashed line shows the $IC_{50}$ value).

According to another aspect of the invention, the antibody is able to bind an epitope of an analyte selected from UR-144 N-pentanoic acid, UR-144 N-(5-hydroxypentyl), UR-144 N-(4-hydroxypentyl) and 1-(tetrahydropyran-4-ylmethyl)-1H-indol-3-yl]-(2,2,3,3-tetramethylcyclopropyl)methanone (A-834735 shown in FIG. 5 (j)).

According to all embodiments of the invention R of structure (I) may be selected from H, substituted methyl, substituted ethyl, substituted or unsubstituted propyl, substituted or unsubstituted butyl, substituted or unsubstituted pentyl or substituted or unsubstituted hexyl.

Preferably, R is a substituted hydrocarbon chain, such as a substituted alkyl group.

According to an embodiment of the invention, R is a substituted pentyl group, optionally selected from 5-hydroxypentyl, 4-hydroxypentyl, pentanoic acid or 5-fluoropentyl.

According to a most preferred embodiment of the invention, R of structure (I) may be pentanoic acid or an amide or ester derivative thereof. For example, R may be pentanoic acid or pentanoic acid HTCL (homocysteine thiolactone).

Alternatively, R is a substituted methyl group. Preferably, methyl is substituted with a substituted or substituted, saturated or unsaturated pyran. According to a preferred embodiment, methyl is substituted with tetrahydropyran. In this manner, R may be $CH_2$—$C_5H_{10}O$ ($CH_2$-tetrahydropyran). This embodiment is disclosed in FIG. 5 (j) as A-834,735.

According to all embodiments of the invention, the antigenicity-conferring carrier material (accm) may be selected from a protein, a protein fragment, a synthetic polypeptide or a semi-synthetic polypeptide.

Optionally, the accm is selected from bovine serum albumin (BSA), egg ovalbumin, bovine gamma globulin, bovine thyroglobulin (BTG), keyhole limpet haemocyanin (KLH). Further optionally, the accm is selected from BSA or BTG. Optionally, the accm is selected from BTG.

Alternatively, the accm comprises synthetic poly(amino acids) having a sufficient number of available amino groups, such as lysine. Further alternatively, the accm is selected from synthetic or natural polymeric materials bearing reactive functional groups. Still further alternatively the accm is selected from carbohydrates, yeasts and polysaccharides.

According to a preferred embodiment of the invention, R of structure (I) is pentanoic acid and the accm is bovine thyroglobulin (BTG), It will be understood that the hapten (i.e., formula (I)) may be directly conjugated or directly coupled to the antigenicity-conferring carrier material (accm). In this case, UR-144 N-pentanoic acid may be directly coupled to the accm via a peptide bond, utilising a carbodiimide compound such as N, N-dicyclohexylcarbodiimide (DCC) to facilitate the reaction. These carbodiimides (such as EDC or DCC) facilitate the reaction between the carboxyl group ($CO_2H$ of R) on the hapten and free amino groups on the accm to form peptide bonds with no crosslinking groups present between the conjugated molecules. In this manner direct coupling takes place via amide bond formation. In this manner, the accm is conjugated directly to R of Structure I.

Alternatively, the hapten (i.e., formula (I)) may be attached to the antigenicity-conferring carrier material (accm) via a cross-linking group or cross linker. The cross-linking group may be any conventional cross linking group conventionally used in this field. The cross-linking group is ideally a functionalised linking group joining the accm to the hapten. Preferably, the cross linking group may be selected from a carboxyl, dithiopyridyl, maleimidyl, amino, hydroxyl, thiol and aldehyde moiety. The cross linking group is well known to the skilled man in immunogen synthesis. In this manner, the accm is conjugated via a cross-linking group to R of Structure I.

Optionally, the antibody of the invention is capable of binding to at least one epitope from the group comprising the molecules UR-144, UR-144 pentanoic acid, UR-144 N-pentanol (UR-144 N-(5-hydroxypentyl) metabolite), UR-144 desalkyl and XLR-11. The term 'able to bind to' or "capable of binding" as used herein means that under standard immunoassay conditions, for example as described in 'Immunoassay: A practical guide' by Brian Law, Taylor and Francis Ltd, ISBN 0-203-48349-9, the antibodies will bind to said molecules.

In a further embodiment the antibody is capable of binding to UR-144 N-(5-bromopentyl) analog, UR-144 N-(5-chloropentyl) analog, XLR-11 N-(4-fluoropentyl) isomer, XLR-11 N-(3-fluoropentyl) isomer, XLR-11 N-(2-fluoropentyl) isomer, XLR-11 N-(4-hydroxypentyl) metabolite, XLR-11 N-(4-pentenyl) analog, AB-005, AB-796260, A-834735, AB-005 Azepane isomer and XLR-11 Degradant. Example 10 shows good cross-reactivity with A-834735.

We have advantageously found that the antibody of the invention is specific for at least one epitope of UR-144 N-pentanoic acid and has cross-reactivity to UR-144, UR-144 N-pentanol, UR-144 desalkyl and XLR-11.

Optionally the antibody has 100% cross-reactivity to UR-144 pentanoic acid and greater than 10%, optionally 15%, cross-reactivity to the group comprising of, but not limited to, UR-144, UR-144 N-pentanol, UR-144 desalkyl and/or XLR-11.

Alternatively, the antibody has 100% cross-reactivity to UR-144 N-pentanoic acid and greater than 100% cross-reactivity to UR-144 N-pentanol, (N-(5-hydroxypentyl) and N-(4-hydroxypentyl) derivatives).

Still alternatively, the antibody has 100% cross-reactivity to UR-144 N-pentanoic acid and greater than 25%, optionally greater than 35% cross-reactivity to XLR-11.

Additionally or alternatively the antibody may be characterised in that it shows no significant binding, preferably at 100 ng/ml of cross-reactant as defined in the examples, to JWH-098, JWH-022, JWH-398, JWH-210, JWH-018 (6 hydroxyindole), JWH-018 (5 hydroxyindole), JWH-018 N (5 hydroxypentyl) metabolite, RCS-4, RCS-8, AM-1220, AM-2201, AM-694, AM-1241, JWH-015, JWH-200, JWH-073, JWH-019, JWH-018, JWH-250 or JWH-018 (N-carboxybutyl) metabolite. As used herein the term 'no significant binding' can be understood to mean any low cross-reactivity which would not compromise the assay. Optionally, this corresponds to a cross-reactivity of less than 5% relative to the analyte with greatest cross-reactivity. More preferably the cross-reactivity is less than 4% or 3% and even more preferably the cross-reactivity is less than 2% or 1% relative to the analyte which shows greatest cross-reactivity in the assay.

Still optionally the antibody has 100% cross-reactivity to UR-144 N-pentanoic acid, and greater than 100% cross-reactivity for UR-144 N-(-5-hydroxypentyl metabolite), UR-144 N-(-4-hydroxypentyl metabolite) and A-834735, and greater than 2% cross-reactivity to the group comprising of, but not limited to, UR-144, XLR-11, UR-144 desalkyl, XLR-11 degradant and/or XLR11 N-(4-hydroxypentyle metabolite).

Additionally or alternatively the antibody may be characterised in that it has an $IC_{50}$ selected from one or more of at least 3 ng/ml, preferably 3.484 ng/ml for UR-144 N-pentanoic acid; at least 22 ng/ml, preferably 22.815 ng/ml for UR-144; at least 3 ng/ml, preferably 3.191 ng/ml for UR-144 N-pentanol; at least 19 ng/ml, preferably 19.207 ng/ml for UR-144 desalkyl; and at least 9 ng/ml, preferably 9.454 ng/ml for XLR-11.

Figure 3:
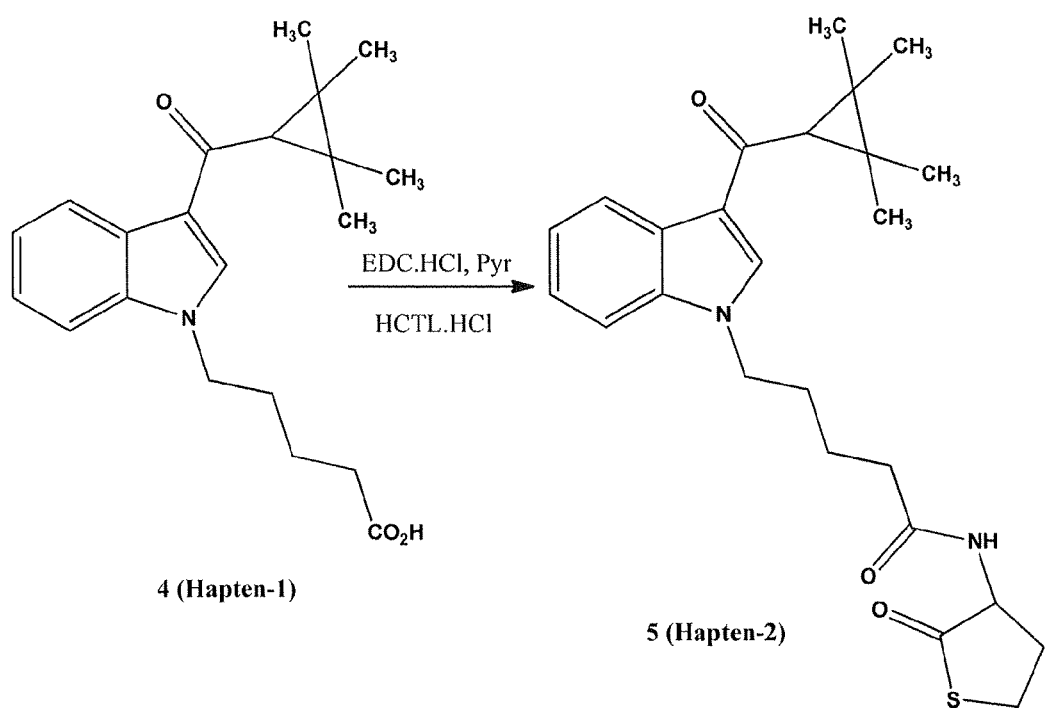
FIG. 3: Chemical reactions for the synthesis of UR-144 N-Pentanoic Acid HCTL (Hapten-2)

It will be understood that the antibodies of the invention are being raisable against or derivable from an immunogen conjugated through the N-position of a cyclopropylindole structure. Preferred immunogens correspond to haptens 1 and 2 as shown in FIG. 3 conjugated to an accm (antigenicity conferring carrier material).

Immunogen I as used herein refers to hapten 1 (UR-144 N-pentanoic acid) conjugated to an accm.

Immunogen II as used herein refers to hapten 2 (UR-144 N-pentanoic acid Homocysteine thiolactone (HCTL)) conjugated to an accm.

As mentioned above, the hapten, such as those of FIG. 3, may be directly conjugated to an accm or they may be conjugated to the accm via a cross-linking group as defined previously.

Optionally, the antigenicity conferring carrier material (accm) is as defined previously and optionally selected from bovine serum albumin (BSA), egg ovalbumin, bovine gamma globulin, bovine thyroglobulin (BTG), keyhole limpet haemocyanin (KLH), synthetic poly(amino acids) having a sufficient number of available amino groups, lysine, and/or synthetic or natural polymeric materials bearing reactive functional groups. Preferably, the accm is bovine thyroglobulin (BTG) or bovine serum albumin (BSA).

It has been found that immunogens of the invention raise antibodies that are able to bind to several cyclopropylindole based molecules including UR-144, XLR-11 and metabolites or derivatives thereof. Exemplary metabolites of UR-144 and XLR-11 are shown in FIGS. 4 and 5. The skilled person is aware that for these antibodies to recognise these molecules they must bind to particular structures or at least one epitope of the hapten (in this context the hapten being that part of the immunogen that is not the cross-linker or accm). The epitopes are often distinct groups incorporating functional groups.

In a preferred embodiment, the antibodies are polyclonal antibodies. However, the skilled person will understand that any type of immunoglobulin molecule or fragment thereof can be used, for example monoclonal antibodies, Fab fragments, scFv fragments and any other antigen binding fragments all of which fall within the scope of the current invention. The polyclonal antibodies may be produced by any method as known to those skilled in the art. Any suitable host animal may be used, preferably a mammalian animal for example, but not limited to sheep, rabbit, mouse, guinea pig or horse. In addition, the antibodies may be in the form of polyclonal antisera.

A further aspect of the invention is an assay method of detecting or determining UR-144, XLR-11 and/or metabolites thereof in an in vitro sample from an individual or in a solution derived from a substance suspected to contain synthetic cannabinoids, the method comprising contacting the sample or solution with at least one detecting agent and at least one antibody of the invention; detecting or determining the detecting agent(s); and deducing from a calibration curve the presence of, or amount of, UR-144, XLR-11 or metabolites in the sample or solution.

'Detecting' as referred to herein means qualitatively analyzing for the presence or absence of a substance, while 'determining' means quantitatively analyzing for the amount of a substance. The detecting agent is a small molecule (generally of similar structure to a molecule to be detected), conjugated to a labelling agent that is able to bind to one of the antibodies of the invention. Sometimes the detecting agent can be referred to as the conjugate. The labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material. For the purposes of the invention, the patient sample to be used for in vitro analysis can be hair or a peripheral biological fluid but is preferably whole blood, serum, plasma, or urine.

Preferably the conjugate or detecting agent used in the immunoassays of the current invention is of the structure II:

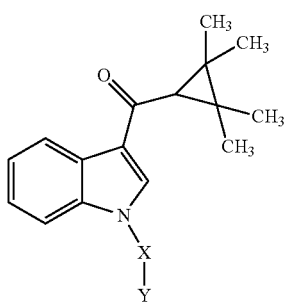

Structure II

In which X is an organic spacing group and Y is a labelling agent which is detectable.

Preferably, the organic spacing group X is -Q-Z—, in which Z, attached to N, is a crosslinking group selected from a $C_1$-$C_{10}$, preferably a $C_1$-$C_5$, substituted or unsubstituted straight or branched chain, saturated or unsaturated alkylene moiety and Q is, before conjugation to Y, a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof.

Preferably the labelling agent is horseradish peroxidase (HRP). Other conventional labelling agents may be used selected from an enzyme, such as peroxidase, a luminescent substance, a radioactive substance or a mixture thereof.

According to a preferred embodiment of the invention, X of structure (II) is pentanoic acid and Y is horseradish peroxidase (HRP).

In a preferred immunoassay of the current invention an immunoassay method is provided for the detection or determination of UR-144, UR-144 pentanoic acid, UR-144 N-pentanol, UR-144 desalkyl or XLR-11 and/or metabolites thereof in a sample, comprising the steps of providing a mixture of the sample, an antibody of the invention and a conjugate or detecting agent of the invention; allowing the antibody to bind to the conjugate and UR-144, UR-144 pentanoic acid, UR-144 N-pentanol, UR-144 desalkyl or XLR-11 and/or metabolites thereof present in the sample; and detecting the presence of or measuring the amount of conjugate bound to the antibody, the presence or amount of conjugate indicating the presence or amount of UR-144, UR-144 pentanoic acid, UR-144 N-pentanol, UR-144 desalkyl or XLR-11 and/or metabolites thereof in the sample.

Optionally, the immunoassay of the current invention can also detect or determine UR-144 N-(5-bromopentyl) analog, UR-144 N-(5-chloropentyl) analog, XLR-11 N-(4-fluoropentyl) isomer, XLR-11 N-(3-fluoropentyl) isomer, XLR-11 N-(2-fluoropentyl) isomer, XLR-11 N-(4-hydroxypentyl) metabolite, XLR-11 N-(4-pentenyl) analog, AB-005, AB-796260, A-834735, AB-005 Azepane isomer, and XLR-11 Degradant.

Another aspect of the invention is a kit for detecting or determining UR-144, XLR-11 or metabolites in a sample, the kit comprising at least one antibody and/or at least one detecting agent of the invention. The kit may comprise one or more antibodies of the invention and one or more additional antibodies with different molecular specificities, i.e., these additional antibodies do not bind to the same structural epitopes as the antibodies of the invention. The additional antibodies may for example detect or determine other synthetic cannabinoid families such as the JWH family. Such an arrangement enables a multiplexing approach to the detection or determination of drugs of abuse. The skilled person in the field of immunodiagnostics will be aware of several alternative immunoassay formats that could incorporate the antibodies of the invention either in solution or attached (e.g., covalently bonded or electrostatically 'non-bonded' through van der Waal's forces) to a solid substrate such as beads, glass/plastic slides or a chip (a chip defined as a small, planar substrate). A preferred solid substrate onto which antibodies of the current invention are covalently bonded is a chip, most preferably a ceramic chip. Such a chip with antibodies attached can be referred to as a biochip' as described in EP1273349, incorporated herein by reference in its entirety. Thus the invention also provides a biochip comprising antibodies of the current invention for the detection and/or determination of UR-144, XLR-11 and metabolites/related molecules.

According to a preferred embodiment, there is provided a kit comprising an antibody of the invention.

Optionally, the kit may further comprising the conjugate of Structure II

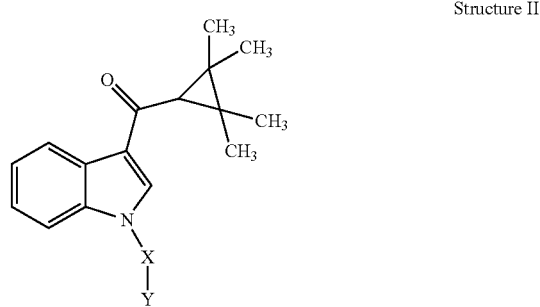

Structure II in which X is an organic spacing group and Y is a labelling agent which is detectable.

Still optionally, the kit may comprise the antibody of the invention which is capable of binding to at least one epitope of an analyte selected from UR-144, UR-144 pentanoic acid, UR-144 N-pentanol, UR-144 desalkyl, XLR-11 and/or metabolites or derivatives thereof.

Methods and Examples

General Methodology
Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOFMS).

General Procedure for MALDI-TOF Analysis of Immunogens.

MALDI-TOF mass spectrometry can be performed using a Voyager STR Biospectrometry Research Station laser-desorption mass spectrometer coupled with delayed extraction. An aliquot of each sample to be analysed can be diluted in 0.1% aqueous trifluoroacetic acid (TFA) to create 1 mg/ml sample solutions. Aliquots (1 µl) can be analysed using a matrix of sinapinic acid and bovine serum albumin (Fluka) as an external calibrant.

Preparation of Antisera

In order to generate polyclonal antisera, 2 mg of an immunogen of the present invention is prepared in PBS, mixed at a ratio of 50% Immunogen in PBS with 50% Freund's Complete adjuvant (Sigma, Product Number—F5881) and emulsified by repeatedly passing the mixture through a tip on the end of a 1 ml syringe, until it reaches the required semi-solid consistency. 1 ml of the mixture is then injected into a host animal, such as rabbit, sheep, mouse, guinea pig or horse. Sheep are the preferred host animal. Further injections (boosts) are administered on a monthly basis (1 mg of immunogen is prepared in PBS and mixed at a ratio of 50% Immunogen in PBS with 50% of Freund's Incomplete Adjuvant, Sigma product Number—F5506) until the required titre is achieved. Serum is sampled for evaluation of the antibody titre.

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Samples are then centrifuged at 4200 rpm for 30 minutes at 4° C. The serum is poured off and centrifuged again, at 10,000 rpm for 15 minutes at 4° C., before being aliquoted and stored at <−20° C.

The Immunoglobulin (Ig) fraction is extracted from the antisera via caprylic acid/ammonium sulphate precipitation of immunoglobulin.

The antibody titre is evaluated by coating a microtitre plate (Thermo Fisher Scientific NUNC, 468667) with antibody (125 µl/well) in coating buffer (10 mM Tris pH 8.5) at 37° C. for 2 hours. The plate is then washed 4 times over 10 minutes with working strength TBST. 50 µl of sample/standard (UR-144 N-Pentanoic acid) is added to the appropriate wells in triplicate, followed by 75 µl of hapten-HRP conjugate and incubated at 25° C. for 1 hour. The plate is then washed and 125 µl of TMB (Randox, 4380-15) added to each well and left at room temperature for 20 mins in the dark. The reaction is stopped using 125 µl of 0.2 M sulphuric acid. The absorbances are read at 450 nm with an ELISA microplate reader (BIO-TEK Instruments, Elx800) and the means calculated. Antibody sensitivity can then be determined.

When the optimal titre has been attained, the host animal is bled to yield a suitable volume of specific antiserum (overall this results in 20 bleeds in total, with approximately 200 ml of antiserum achieved per bleed). The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Various purification steps are available if required, including Immunoglobulin Precipitation (as described above), Antigen-specific affinity purification, Size-exclusion chromatography and Ion Exchange Chromatography.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal antibodies.

This can be carried out using an ELISA based format as described above for measuring antibody titre or as a Biochip based format. Details of how the antibodies are fixed to the Biochip are described in FitzGerald, S. P. et al, Clin. Chem. 51(7); 1165-1176; 2005. The signal emitted in the immunoassay is proportionate to the amount of detecting agent bound to the antibodies which in turn is inversely proportionate to the analyte concentration. The signal can be detected or quantified by comparison with a calibrator.

Figure 2:
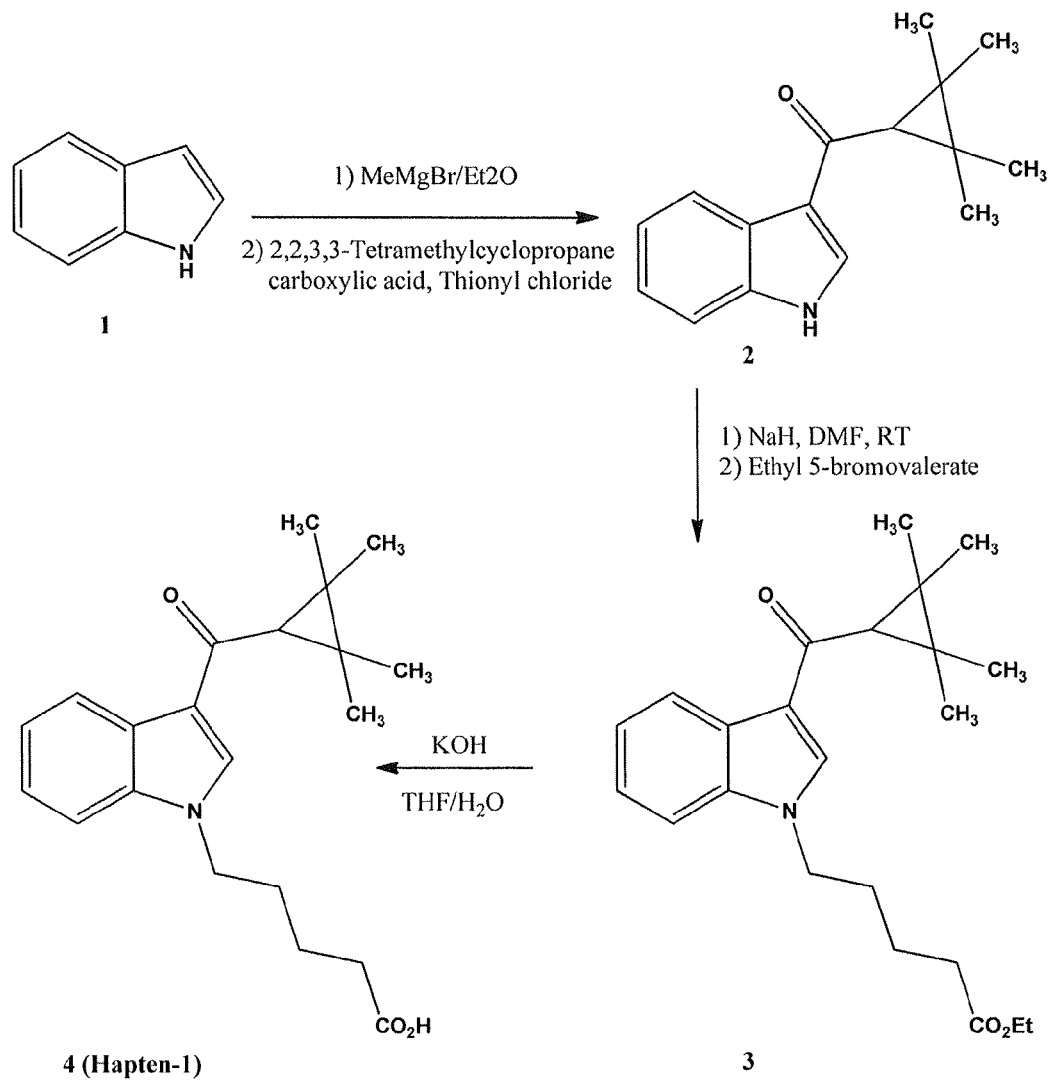
FIG. 2: Chemical reactions for the synthesis of UR-144 N-Pentanoic Acid (Hapten-1)

EXAMPLES (Numbers in bold refer to structures in FIG. 2 or FIG. 3)

Example 1

Preparation of N-Desalkyl UR-144 2

Indole 1 (11.7 g, 100 mmol) was dissolved in diethylether (100 ml) under nitrogen atmosphere and cooled to 0° C. 3M solution of MeMgBr (35 ml, 105 mmol) was added drop-wise and allowed to stir at room temperature for 3 hours. In the meantime, 2,2,3,3-tetramethylcyclopropane carboxylic acid (14.22 g, 100 mmol) was dissolved in thionyl chloride (100 ml) and refluxed for 90 min, then the solvent was removed under vacuo and the residue was dissolved in diethylether (100 ml). The resulting solution was added drop-wise to the indole reaction mixture at 0° C. and then allowed to stir at room temperature for 2 hours. A solution of ammonium chloride (200 ml) was added to the reaction mixture and the resulting mixture was stirred at room temperature overnight. The reaction mixture was extracted with ethyl acetate (3×200 ml). The combined organic extracts were washed by water, brine, dried over sodium sulfate, filtered and evaporated to dryness. The crude was purified by column chromatography (silica gel: 10-30% ethyl acetate in hexane) to give 8.6 g (36%) of N-desalkyl UR-144 2 as a cream solid.

Example 2

Preparation of UR-144 N-Pentanoic Acid Ethyl Ester 3

60% Sodium hydride in mineral oil (597 mg, 12.43 mmol) was suspended in dimethylformamide (25 ml) and n-desalkyl UR-144 2 (3 g, 5.54 mmol) was added portion wise at room temperature and the mixture was stirred for a further 30 min at room temperature after the addition was finished. Ethyl 5-bromovalerate (2.95 ml, 18.65 mmol) in dimethylformamide (10 ml) was added drop wise at room temperature and the reaction mixture was stirred at room temperature overnight. Solvents were removed in vacuo and the residue was partitioned between ethyl acetate (200 ml) and water (150 ml). The layers were separated and aqueous layer was extracted 2 times with ethyl acetate (2×100 ml). All the organic layers were combined, washed by water, brine, dried over sodium sulfate and evaporated to dryness. The residue obtained was purified by column chromatography (silica gel, 20% ethyl acetate in hexane) to give 3.68 g (80%) UR-144 N-pentanoic acid ethyl ester 3 as an oil.

Example 3

Preparation of UR-144 N-Pentanoic Acid 4 (Hapten-1)

UR-144 N-pentanoic acid ethyl ester 3 (3.68 g, 9.96 mmol) was dissolved in a mixture of tertahydrofuran (30 ml) and water (30 ml), to this solution was added potassium hydroxide (1.31 g, 19.92 mmol). The reaction mixture was stirred at room temperature overnight. The solvent was removed in vacuo; the residue was acidified to pH 3 and extracted three times with a mixture 1:1 ethyl acetate:tetrahydrofuran (3×100 ml). The organic fractions were combined, washed by water, dried over sodium sulfate and evaporated to dryness. The residue was purified by column chromatography (silica gel, ethyl acetate) to give 2.5 g (74%) of UR-144 N-pentanoic acid 4 (Hapten-1) as a white solid.

NMR 13C (DMSO-d6): 194.358; 175.099; 137.218; 136.515; 126.696; 123.407; 122.688; 122.467; 119.337; 111.301; 46.633; 42.949; 33.968; 31.643; 29.902; 24.499 (2C); 22.646 and 17.913 (2C).

Example 4

Preparation of UR-144 N-Pentanoic Acid HCTL 5 (Hapten-2)

To a solution of UR-144 N-pentanoic acid 4 (Hapten-1) (355 mg, 1.02 mmol) in pyridine (5 ml) were added homocysteine thiolactone hydrochloride (235 mg, 1.53 mmol) and EDC hydrochloride (293 mg, 1.53 mmol) and the mixture stirred at room temperature overnight. Solvent was removed in vacuo and the crude residue was partitioned between water (10 ml) and ethyl acetate (25 ml). The layers were separated and aqueous layer was extracted with ethyl acetate (2×25 ml). All the organic layers were combined, washed by water, brine, dried over sodium sulfate and evaporated to dryness. The crude mixture obtained was purified by chromatography (silica gel: 50-80% ethyl acetate in hexane) to give UR-144 N-pentanoic acid HCTL 5 (Hapten-2) (354 mg, 78%) as a cream amorphous solid.

Example 5

Conjugation of UR-144 N-Pentanoic Acid 4 (Hapten-1) to BSA

To a solution of UR-144 N-pentanoic acid 4 (hapten-2) (13.0 mg, 0.038 mmol) in Dimethylformamide (DMF) (1.0 ml) was added N, N-dicyclohexylcarbodiimide (DCC) (8.53 mg, 0.041 mmol) and N-hydroxysuccinimide (4.76 mg, 0.041 mmol) and the mixture was stirred at room temperature overnight. The dicyclohexylurea formed was removed by filtration and the solution was added drop-wise to a solution of BSA (50 mg, 1.5 µmol) in 50 mM sodium bicarbonate solution (pH 8.5) (5 ml). The mixture was then stirred overnight at 4° C. The solution was then dialysed against 50 mM phosphate buffer pH 7.2 (3 changes) for 24 hours at 4° C., and freeze-dried.

MALDI results showed 21.2 molecule of hapten-1 had been conjugated to one molecule of BSA.

Example 6

Conjugation of UR-144 N-Pentanoic Acid 4 (Hapten-1) to BTG

To a solution of UR-144 N-Pentanoic Acid 4 (hapten-1) (46.1 mg, 0.135 mmol) in Dimethylformamide (DMF) (1.0 ml) was added N,N-dicyclohexylcarbodiimide (DCC) (33.4 mg, 0.162 mmol) and N-hydroxysuccinimide (18.64 mg, 0.162 mmol) and the mixture was stirred at room temperature overnight. The dicyclohexylurea formed was removed by filtration and the solution was added drop-wise to a solution of BTG (150 mg) in 50 mM sodium bicarbonate solution (pH 8.5) (5 ml). The mixture was then stirred overnight at 4° C. The solution was then dialysed against 50 mM phosphate buffer pH 7.2 (3 changes) for 24 hours at 4° C., and freeze-dried.

Example 7

Conjugation of UR-144 N-Pentanoic Acid 4 (Hapten-1) to HRP

EDC hydrochloride (10 mg) was dissolved in water (0.5 ml) and immediately added to a solution of UR-144 N-pentanoic acid 4 (hapten-1) (2 mg) in Dimethylformamide (DMF) (0.2 ml). After mixing, this solution was added drop-wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 8

Conjugation of UR-144 N-Pentanoic Acid HCTL 5 (Hapten-2) to Maleimide Modified-HRP A solution of p-Maleimidomethylcyclohexyl-1-carboxylic acid NHS ester (1.84 mg) in Dimethylformamide (DMF) (0.045 ml) was added drop-wise to a solution of HRP (20 mg) in 50 mM HEPES buffer (0.8 mL) while stirring. And then the resulting solution was stirred at room temperature for 40 minutes. Excess p-maleimidomethylcyclohexyl-1-carboxylic acid NHS ester was removed by dialysis against Phosphate Buffered Saline, pH 7.2 in the dark.

UR-144 N-pentanoic acid HCTL (hapten-2) (2 mg) was dissolved in Dimethylformamide (DMF) (0.2 mL). 0.2 mL of 1M potassium hydroxide solution was added to the above hapten solution and the mixture was stirred for 10 minutes at room temperature. And then 0.5 mL of 0.2 M Phosphate Buffer, pH 7.0 was added to quench the reaction; 0.15 mL of HCL solution (1M) was added to bring the pH to 7.0. This solution was added drop-wise to the solution of maleimide modified HRP and the mixture was rolled for 2 hours at RT and overnight at 4° C. Excess hapten was removed with PD-10 column (Pharmacia), pre-equilibrated with Phosphate Buffered Saline pH 7.2, followed by dialysis at 2-8° C. against the same buffer.

Example 9

Characterization of Antibodies to Immunogens I and II

The wells of an enhanced binding 96 well polystyrene microtiter plate were coated with IgG fraction of antiserum raised to Immunogen I or II, diluted in 10 mM Tris, pH 8.5 (125 µl/well). The appropriate antibody coating dilution was determined using standard ELISA checkerboard techniques. The plate was incubated overnight at 4° C., washed 4 times over 10 minutes with Tris buffered saline containing Tween20 (TBST) and tapped dry. Standard solutions (UR-144 N-pentanoic acid) were applied at 0, 0.625, 1.25, 2.5, 5, 10, 20 and 40 ng/ml and 50 µl of each was added to the appropriate wells. 75 µl of conjugate (appropriate hapten-HRP) diluted in Tris buffer (pH 7.2) containing EDTA, D-mannitol, sucrose, thimerosol and BSA, was added to each of the wells. The appropriate dilution of conjugate was also determined using standard ELISA checkerboard techniques. The plate was incubated at 25° C. for 1 hour. Excess unbound conjugate was removed by washing 6 times over a ten minute period with TBST. 125 µl of tetramethylbenzidine (TMB) substrate solution was added to each well of the plate that was then incubated for 20 minutes in the dark at room temperature. The reaction was terminated by addition of 125 µl of 0.2 M $H_2SO_4$ to each well. The absorbance was then measured at 450 nm using a microtiter plate reader. The data are inputted to a computer program called 'KC Junior' (Biotek). It gives a 4 parameter fit curve and allows the calculation of concentrations between the standard runs. This program is used to calculate the $IC_{50}$ values by dividing the 0 ng/ml optical density (OD) value by 2 and obtaining the concentration value from the curve for this OD.

Cross-reactivity was calculated according to the following formula:

$$\% CR = IC_{50,\ UR\text{-}144\ N\text{-}pentanoic\ acid}/IC_{50,\ cross\ reactant} \times 100$$

Where % CR is the percentage cross-reactivity, $IC_{50,\ UR\text{-}144\ N\text{-}pentanoic\ acid}$ is the concentration of UR-144 N-pentanoic acid that causes 50% displacement of signal and $IC_{50,\ cross\ reactant}$ is the concentration of the cannabinoid/metabolite/selected molecule that causes 50% displacement of signal.

The data generated from this assay using antiserum raised to Immunogen I is presented in Table 1.

The antiserum used to generate this data was taken from the second bleed of up to twenty total bleeds which may be taken and hence antibody sensitivity is anticipated to improve from subsequent bleeds.

TABLE 1

Antibody characterisation using antiserum raised to Immunogen I and detecting agent derived from hapten 1 in a competitive assay format (CR based on 100% for UR-144 N-pentanoic acid).

| Analyte | % B/BO | $IC_{50}$ (ng/ml) | % Cross-reactivity (CR) |
|---|---|---|---|
| UR-144 N-pentanoic acid | 16.8 | 3.484 | 100 |
| UR-144 | 40.5 | 22.815 | 15.3 |
| UR-144 N-pentanol | 13.0 | 3.191 | 109.2 |

TABLE 1-continued

Antibody characterisation using antiserum raised to Immunogen I and detecting agent derived from hapten 1 in a competitive assay format (CR based on 100% for UR-144 N-pentanoic acid).

| Analyte | % B/BO | $IC_{50}$ (ng/ml) | % Cross-reactivity (CR) |
|---|---|---|---|
| UR-144 desalkyl | 38.5 | 19.207 | 18.1 |
| XLR-11 | 24.0 | 9.454 | 36.9 |

B = absorbance at 450 nm at x ng/ml standard concentration
$B_0$ = absorbance at 450 nm at 0 ng/ml standard concentration
$IC_{50}$ = standard concentration which produces 50% $B/B_0$ Cross Reactivity In order to determine the specificity of the competitive ELISAs, standard solutions of a range of structurally related synthetic cannabinoids and their metabolites were prepared in TBST (Tris-Buffered Saline and Tween 20). Using the calibration curves generated and employing a single level of cross reactants, these were used to determine the cross-reactivity of the immunoassays with these substances. The results of this study are presented in Table 2. Table 3 shows the identity of the compounds used.

TABLE 2

Cross reactivity of the competitive ELISAs for related synthetic cannabinoid molecules

| Cross-Reactant (100 ng/ml) | % B/BO | $IC_{50}$ (ng/ml) | % Cross-reactivity (CR) |
|---|---|---|---|
| JWH-081 | 97.10 | >100 | <3.0 |
| JWH-122 | 97.01 | >100 | <3.0 |
| JWH-098 | 93.94 | >100 | <3.0 |
| JWH-022 | 91.83 | >100 | <3.0 |
| JWH-398 | 88.86 | >100 | <3.0 |
| JWH-210 | 95.89 | >100 | <3.0 |
| JWH-018 (6 hydroxyindole) | 93.92 | >100 | <3.0 |
| JWH-018 (5 hydroxyindole) | 94.61 | >100 | <3.0 |
| JWH-018 N (5 hydroxypentyl) metabolite | 87.56 | >100 | <3.0 |
| RCS 4 | 80.02 | >100 | <3.0 |
| RCS 8 | 88.15 | >100 | <3.0 |
| AM1220 | 73.59 | >100 | <3.0 |
| AM2201 | 85.58 | >100 | <3.0 |
| AM694 | 79.00 | >100 | <3.0 |
| AM1241 | 77.96 | >100 | <3.0 |
| JWH-015 | 89.77 | >100 | <3.0 |
| JWH-200 | 86.38 | >100 | <3.0 |
| JWH-073 | 90.44 | >100 | <3.0 |
| JWH-019 | 87.30 | >100 | <3.0 |
| JWH-018 | 87.89 | >100 | <3.0 |
| JWH-250 | 85.90 | >100 | <3.0 |
| JWH-018 N (carboxybutyl) metabolite | 89.14 | >100 | <3.0 |

TABLE 3

Identity of cross-reactants by CAS registry number

| Cross-Reactant | CAS registry number |
|---|---|
| JWH-081 | 210179-46-7 |
| JWH-122 | 619294-47-2 |
| JWH-098 | 316189-74-9 |
| JWH-022 | 209414-16-4 |
| JWH-398 | 1292765-18-4 |
| JWH-210 | 824959-81-1 |
| JWH-018 (6 hydroxyindole) | 1307803-44-6 |
| JWH-018 (5 hydroxyindole) | 335161-21-2 |

TABLE 3-continued

Identity of cross-reactants by CAS registry number

| Cross-Reactant | CAS registry number |
|---|---|
| JWH-018 N (5 hydroxypentyl) metabolite | NA |
| RCS 4 | 1345966-78-0 |
| RCS 8 | 1345970-42-4 |
| AM1220 | 137642-54-7 |
| AM2201 | 335161-24-5 |
| AM694 | 335161-03-0 |
| AM1241 | 444912-48-5 |
| JWH-015 | 155471-08-2 |
| JWH-200 | 103610-04-4 |
| JWH-073 | 208987-48-8 |
| JWH-019 | 209414-08-4 |
| JWH-018 | 209414-07-3 |
| JWH-250 | 864445-43-2 |
| JWH-018 N (carboxybutyl) metabolite | NA |

NA = not available

Example 10

A further assay was carried out in accordance with the protocol described in Example 9 using Immunogen I.

The data generated from this assay using antiserum raised to Immunogen I is presented in Table 4.

The antiserum used to generate this data was taken from the third bleed of up to twenty total bleeds which may be taken. Specificity

TABLE 4

The specificity of the UR144/XLR11 Synthetic Cannabinoids (Spice) ELISA:

| Cross-Reactivity of UR144/XLR11 Synthetic Cannabinoid compounds | |
|---|---|
| Compound | % Cross-Reactivity |
| UR144 N-Pentanoic Acid | 100 |
| A-834735 | 111 |
| UR144 N-(5-hydroxypentyl) metabolite | 110 |
| UR144 N-(4-hydroxypentyl) metabolite | 107 |
| XLR11 | 29 |
| UR144 | 19 |
| UR144 Desalkyl | 13 |
| XLR11 Degradant | 3 |
| XLR11 N-(4-hydroxypentyl) metabolite | 2 |

| Concentration of compounds that elicit a negative response | |
|---|---|
| Compound | ng/mL |
| JWH-018 adamantyl carboxamide | 10 |
| JWH-018 adamantyl (AB001) | 100 |
| AB001N-pentanoic acid | 100 |
| AB001 N-pentanol | 100 |
| N-desalkyl AB001 | 100 |
| 2-OH JWH-018 (JWH-018 2-hydroxyindole metabolite) | 100 |
| 4-OH JWH-018 (JWH-018 4-hydroxyindole metabolite) | 100 |
| 5-OH JWH-018 (JWH-018 5-hydroxyindole metabolite) | 100 |
| 6-OH JWH-018 (JWH-018 6-hydroxyindole metabolite) | 100 |
| 7-OH JWH-018 (JWH-018 7-hydroxyindole metabolite) | 100 |
| N-desalkyl JWH-018 (other name (3-(1-naphthoyl) indole) | 100 |
| JWH-018 N-(4-hydroxypentyl) metabolite (other name 1-(4-hydroxypentyl)-1H-indol-3-yl(napthalen-1-yl)-methanone) | 100 |
| JWH-018 N-(5-hydroxypentyl) metabolite (other name 1-(5-hydroxypentyl)-1H-indol-3-yl(naphthalen-1-yl)methanone) | 100 |
| JWH-018 N-pentanoic acid metabolite (other name 5-(3-(1-naphthyl)-1H-indol-1-yl)pentanoic acid) | 100 |
| JWH-073 | 100 |
| 2-OH JWH-073 (JWH-073 2-hydroxyindole metabolite) | 100 |
| 4-OH JWH-073 (JWH-073 4-hydroxyindole metabolite) | 100 |
| 5-OH JWH-073 (JWH-073 5-hydroxyindole metabolite) | 100 |
| 6-OH JWH-073 (JWH-073 6-hydroxyindole metabolite) | 100 |
| 7-OH JWH-073 (JWH-073 7-hydroxyindole metabolite) | 100 |
| JWH-073 N-(3-hydroxybutyl) metabolite (other name 1-(3-hydroxybutyl)-1H-indol-3-yl(napthalen-1-yl)methanone) | 100 |
| JWH-073 N-(4-hydroxybutyl) metabolite (other name 1-(4-hydroxybutyl)-1H-indol-3-yl(naphthalen-1-yl)methanone) | 100 |
| JWH-073 N-butanoic acid metabolite (other name 4-(3-(1-naphthyl)-1H-indol-1-yl)butanoic acid) | 100 |
| JWH-015 | 100 |
| JWH-019 5-hydroxyindole metabolite (JWH-019-M2) | 100 |
| JWH-022 | 100 |
| JWH-081 | 100 |
| JWH-081 N-(5-hydroxypentyl) metabolite | 100 |
| JWH-098 | 100 |
| JWH-122 | 100 |
| JWH-200 (other name WIN 55, 225) | 100 |
| JWH-250 | 100 |
| JWH-250 N-(5-hydroxypentyl) metabolite | 100 |
| JWH-250 N-(5-carboxypentyl) metabolite | 100 |
| JWH-398 | 100 |
| AM-694 | 100 |
| AM-1241 | 100 |
| AM-2201 | 100 |
| RCS-4 | 100 |
| RCS-8 (SR-18) | 100 |
| AKB48 N (5-fluoropentyl) analog | 100 |
| STS135 | 100 |

We claim the following:

1. An antibody capable of binding to an epitope having the general formula (I):

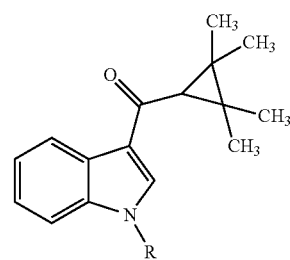

(I)

wherein, R is selected from the group consisting of H, substituted methyl, substituted ethyl, substituted or unsubstituted propyl, substituted or unsubstituted butyl, substituted or unsubstituted pentyl, and substituted or unsubstituted hexyl, wherein the antibody has 100% cross-reactivity to UR-144 pentanoic acid, and compared to said cross-reactivity to said UR-144 pentanoic acid, the antibody has greater than 10% cross-reactivity to UR-144, UR-144 N-pentanol, UR-144 desalkyl and XLR-11, and wherein the antibody shows no significant binding to JWH-098, JWH-022, JWH-398, JWH-210, JWH-018 6-hydroxyindole, JWH-018 5-hydroxyindole, RCS-4, RCS-8, AM-1220, AM-2201, AM-694, AM-1241, JWH-015, JWH-200, JWH-073, JWH-019, JWH-018, and JWH-250.

2. The antibody of claim 1 wherein R is a substituted pentyl group.

3. The antibody of claim 1 wherein R is selected from pentyl, 5-hydroxypentyl, 4-hydroxypentyl, pentanoic acid, and 5-fluoropentyl.

4. The antibody of claim 1 wherein R is pentanoic acid or an amide or ester derivative thereof.

5. The antibody of claim 1 wherein R is a substituted methyl group.

6. The antibody of claim 1 wherein R is a substituted methyl group in which methyl is substituted with substituted or substituted, saturated or unsaturated pyran.

7. The antibody of claim 1 wherein R is a substituted methyl group in which methyl is substituted with tetrahydropyran.

8. The antibody of claim 1, wherein the antibody has greater than 15% cross-reactivity to UR-144, UR-144 N-pentanol, UR-144 desalkyl and XLR-11.

9. The antibody of claim 1, wherein the antibody has greater than 100% cross-reactivity to UR-144 N-pentanol.

10. The antibody of claim 1 with an $IC_{50}$ selected from one or more of at least 3.484 ng/ml for UR-144 N-pentanoic acid, 22.815 ng/ml for UR-144, 3.191 ng/ml for UR-144 N-pentanol, 19.207 ng/ml for UR-144 desalkyl and 9.454 ng/ml for XLR-11.

11. An antibody raised against an immunogen, wherein the immunogen comprises formula (I) conjugated to an antigenicity-conferring carrier material (accm):

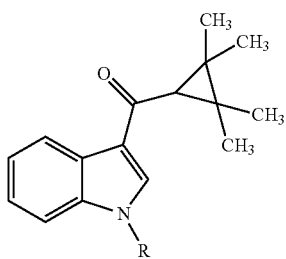

(I)

wherein, R is selected from the group consisting of H, substituted methyl, substituted ethyl, substituted or unsubstituted propyl, substituted or unsubstituted butyl, substituted or unsubstituted pentyl, and substituted or unsubstituted hexyl, and the antibody is able to bind an epitope of an analyte selected from the group consisting of UR-144, UR-144 pentanoic acid, UR-144 N-pentanol, UR-144 desalkyl, XLR-11, and metabolites or derivatives thereof, wherein the antibody has 100% cross-reactivity to the UR-144 pentanoic acid, and compared to said cross-reactivity to said UR-144 pentanoic acid, the antibody has greater than 10% cross-reactivity to the UR-144, UR-144 N-pentanol, UR-144 desalkyl and XLR-11, and wherein the antibody shows no significant binding to JWH-098, JWH-022, JWH-398, JWH-210, JWH-018 6-hydroxyindole, JWH-018 5-hydroxyindole, RCS-4, RCS-8, AM-1220, AM-2201, AM-694, AM-1241, JWH-015, JWH-200, JWH-073, JWH-019, JWH-018, and JWH-250.

12. The antibody of claim 11, wherein the immunogen comprises formula (I) directly conjugated to the antigenicity-conferring carrier material (accm).

13. The antibody of claim 11, wherein the immunogen comprises formula (I) conjugated to the antigenicity-conferring carrier material (accm) via a cross-linking group selected from the group consisting of a carboxyl, dithiopyridyl, maleimidyl, amino, hydroxyl, thiol, and an aldehyde moiety.

14. The antibody of claim 11 wherein the antigenicity-conferring carrier material (accm) is selected from the group consisting of bovine serum albumin (BSA), egg ovalbumin, bovine gamma globulin, bovine thyroglobulin (BTG), keyhole limpet haemocyanin (KLH), synthetic poly(amino acids) having a sufficient number of available amino groups, lysine, and synthetic or natural polymeric materials bearing reactive functional groups.

15. The antibody of claim 11, which is derived from an immunogen consisting of either UR-144 N-pentanoic acid or UR-144 N-pentanoic acid homocysteine thiolactone (HCTL) conjugated to the antigenicity-conferring carrier material.

16. An immunoassay method for detecting or quantifying any one or more of UR-144, UR-144 pentanoic acid, UR-144 N-pentanol, UR-144 desalkyl, XLR-11 and metabolites thereof in a sample, the method comprising the steps of
a) providing a mixture of the sample, the antibody of claim 1 and a conjugate of structure II

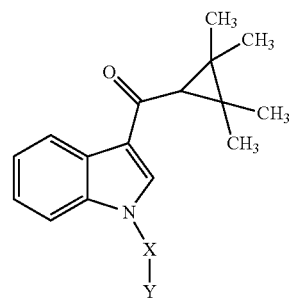

Structure II in which
X is an organic spacing group and Y is a labelling agent which is detectable;
b) allowing the antibody to bind to the conjugate and the any one or more of UR-144, UR-144 pentanoic acid, UR-144 N-pentanol, UR-144 desalkyl, XLR-11, and metabolites thereof present in the sample; and
c) detecting the presence of or measuring the amount of the conjugate bound to the antibody, the presence or amount of the conjugate indicating the presence or amount of the one or more of UR-144, UR-144 pentanoic acid, UR-144 N-pentanol, UR-144 desalkyl, XLR-11 and metabolites thereof in the sample.

17. The immunoassay method of claim 16 wherein X of structure II is -Q-Z—, in which Z, attached to N, is a crosslinking group that is a $C_1$-$C_{10}$, substituted or unsubstituted straight or branched chain, saturated or unsaturated moiety; and Q is (before conjugation to Y) a carboxylic acid or an ester thereof, an aldehyde, an amino group, a maleimide, a halocarboxylic acid or an ester thereof, a dithiopyridyl moiety, a vinylsulphone moiety, or a thiocarboxylic acid or an ester thereof.

18. The immunoassay method of claim 16 wherein Y is selected from the group consisting of an enzyme, a luminescent substance, a radioactive substance and a mixture thereof.

19. An immunoassay method for detecting or quantifying any one or more of UR-144, UR-144 pentanoic acid, UR-144 N-pentanol, UR-144 desalkyl, XLR-11 and metabolites thereof in a sample, the method comprising the steps of
a) providing a mixture of the sample, the antibody of claim 11 and a conjugate of structure II

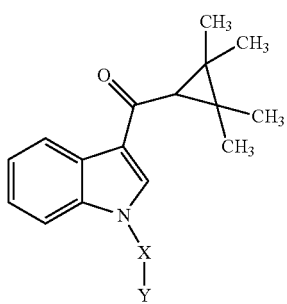

Structure II in which X is an organic spacing group and Y is a labelling agent which is detectable;

b) allowing the antibody to bind to the conjugate and the any one or more of UR-144, UR-144 pentanoic acid, UR-144 N-pentanol, UR-144 desalkyl, XLR-11 and metabolites thereof present in the sample; and c) detecting the presence of or measuring the amount of the conjugate bound to the antibody, the presence or amount of the conjugate indicating the presence or amount of the any one or more of UR-144, UR-144 pentanoic acid, UR-144 N-pentanol, UR-144 desalkyl, XLR-11 and metabolites thereof in the sample.

20. The immunoassay method of claim 19 wherein X of structure II is -Q-Z—, in which Z, attached to N, is a crosslinking group that is a $C_1$-$C_{10}$, substituted or unsubstituted straight or branched chain, saturated or unsaturated moiety; and Q is (before conjugation to Y) a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof.

21. The immunoassay method of claim 19 wherein Y is selected from the group consisting of an enzyme, a luminescent substance, a radioactive substance, and a mixture thereof.

22. The antibody of claim 1, wherein the antibody has greater than 100% cross-reactivity for UR-144 N-(-5-hydroxypentyl) metabolite, UR-144 N—(-4-hydroxypentyl) metabolite and A-834735, and the antibody has 3% or less cross-reactivity to XLR-11 degradant and XLR11 N—(4-hydroxypentyl) metabolite.

23. The antibody of claim 1, wherein the antibody has a cross-reactivity selected from the group consisting of about 29% cross-reactivity to XLR11, about 19% cross-reactivity to UR144, and about 13% cross-reactivity to UR144 desalkyl.

24. The immunoassay method of claim 17, wherein the $C_1$-$C_{10}$ substituted or unsubstituted straight or branched chain, saturated or unsaturated moiety is a $C_1$-$C_5$ substituted or unsubstituted straight or branched chain, saturated or unsaturated moiety.

25. The immunoassay method of claim 20, wherein the $C_1$-$C_{10}$ substituted or unsubstituted straight or branched chain, saturated or unsaturated moiety is a $C_1$-$C_5$ substituted or unsubstituted straight or branched chain, saturated or unsaturated moiety.

* * * * *